United States Patent [19]

Engel et al.

[11] Patent Number: 4,716,242

[45] Date of Patent: Dec. 29, 1987

[54] SALTS OF OXAZAPHOSPHORINE DERIVATIVES

[75] Inventors: Jürgen Engel, Alzenau; Axel Kleemann, Mühlheim; Ulf Niemeyer; Peter Hilgard, both of Bielefeld; Joerg Pohl, Halle, all of Fed. Rep. of Germany

[73] Assignee: Asta-Werke Aktiengesellschaft Chemische Fabrik, Bielefeld, Fed. Rep. of Germany

[21] Appl. No.: 704,465

[22] Filed: Feb. 22, 1985

[30] Foreign Application Priority Data

Mar. 1, 1984 [DE] Fed. Rep. of Germany ....... 3407585

[51] Int. Cl.$^4$ ................................. C07F 9/40
[52] U.S. Cl. ..................................... 558/81
[58] Field of Search ................ 558/81 U.S. only

[56] References Cited

U.S. PATENT DOCUMENTS

| 4,220,660 | 9/1980 | Brock | 514/578 |
| 4,329,709 | 12/1980 | Sato | 260/974 |
| 4,618,692 | 10/1986 | Scheffler et al. | 558/81 |

FOREIGN PATENT DOCUMENTS

| 2495 | 6/1979 | European Pat. Off. |  |
| 83439 | 7/1983 | European Pat. Off. |  |
| 2552135 | 5/1976 | Fed. Rep. of Germany |  |
| 2921057 | 12/1979 | Fed. Rep. of Germany |  |
| 3133309 | 4/1982 | Fed. Rep. of Germany |  |
| 3111428 | 10/1982 | Fed. Rep. of Germany |  |
| 3133077 | 3/1983 | Fed. Rep. of Germany |  |
| 3132221 | 5/1983 | Fed. Rep. of Germany |  |
| 3247436 | 7/1983 | Fed. Rep. of Germany |  |
| 3220432 | 12/1983 | Fed. Rep. of Germany |  |
| 3220672 | 12/1983 | Fed. Rep. of Germany |  |
| 3505482 | 9/1985 | Fed. Rep. of Germany | 558/81 |

OTHER PUBLICATIONS

Draiger Cancer Treatment Report, vol. 60, No. 4, Apr. 1976, pp. 355–359.
Chemical Abstract, vol. 86 (1977) 89765z.
Chemical Abstract, vol. 92 (1980) 19865p.
Chemical Abstract, vol. 94 (1981) 208918d.

Primary Examiner—Anton H. Sutto

Attorney, Agent, or Firm—Cushman, Darby & Cushman

[57] ABSTRACT

There are provided new antitumor salts of oxazaphosphorine derivatives of the formula

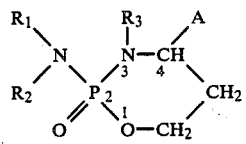

where $R_1$, $R_2$, and $R_3$ are the same or different and represent hydrogen, methyl, ethyl, 2-chloroethyl, or 2-methanesulfonyloxyethyl and wherein at least two of these residues are 2-chloroethyl and/or 2-methanesulfonyl-oxyethyl and A is the group —S—alk—$SO_3H$ or —N(OH)—CONH—alk—$CO_2H$ and alk represents a $C_2$–$C_6$-alkylene residue optionally containing a mercapto group, whereby alk also can be —$CH_2$— in case there is a carboxy group attached to the alk group, with homocysteinethiolactone or $\alpha$-amino-$\epsilon$-caprolactam or a basic compound of the formula:

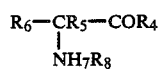

II wherein $R_4$ is a hydroxy group, an amino group or a $C_1$–$C_6$-alkoxy group, $R_5$ is hydrogen or a difluoromethyl group, $R_6$ is hydrogen, an indolyl-(3)-methyl residue, imidazolyl-(4)-methyl residue, a $C_1$–$C_{10}$-alkyl group or a $C_1$–$C_{10}$-alkyl group which is substituted by a hydroxy group, a $C_1$–$C_6$-alkoxy group, a mercapto group, a $C_1$–$C_6$-alkylmercapto group, a phenyl group, a hydroxy phenyl group, an amino-$C_1$–$C_6$-alkylmercapto group, an amino-$C_1$–$C_6$-alkoxy group, an amino group, an aminocarbonyl group, a ureido group ($H_2NCONH$—), a guanidino group or a $C_1$–$C_6$-alkoxycarbonyl group, or wherein $R_6$ together with the structured portion >$CR_5(NR_7R_8)$ forms the proline residue, the 4-hydroxy-proline residue or the 2-oxo-3-amino-3-difluoromethyl-piperidine and the residues $R_7$ and $R_8$ represent hydrogen or $C_1$–$C_6$-alkyl residues.

7 Claims, No Drawings

SALTS OF OXAZAPHOSPHORINE DERIVATIVES

BACKGROUND OF THE INVENTION

In Belgian Pat. No. 892589 there are described oxazaphosphorin-4-thio-alkanesulfonic acids and specific salts thereof of the general formula:

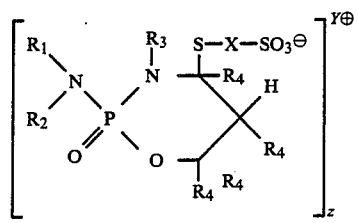

In the preceding formula $R_1$, $R_2$, and $R_3$ which can be the same or different, stand for hydrogen, methyl, ethyl, 2-chloroethyl or 2-methanesulfonyloxyethyl, wherein at least two of those residues are 2-chloroethyl and/or 2-methanesulfonyloxyethyl, $R_4$ is hydrogen or methyl, X is a straight or branched chain $C_2$–$C_6$ alkylene which can have a mercapto group on the 1-, 2-, 3-, 4-, or 5-carbon atoms of the alkylene chain, and $Y^\oplus$ is the hydrogen cation, an alkali or alkaline earth cation, the guanidinium, morpholinium or cyclohexylammonium cation or the cation which is derived from an amine of the formula $NR_5R_6R_7$ wherein the residues $R_5$ to $R_7$ are the same or different and are hydrogen, $C_1$–$C_2$-alkyl groups or hydroxyethyl groups, or $Y^\oplus$ is the ethylenediammonium cation $H_3N^\circ$—$CH_2$—$N^\circ H_3$ or the piperazinonium cation and z is 1 where $Y^\circ$ is a monobasic cation, or z is 2 where $Y^\oplus$ is a dibasic cation of the cation of a compound having two monobasic cations.

Furthermore, the German published application No. 3133309 concerns 4-carbamoyloxyoxaphosphorine derivatives of the general formula

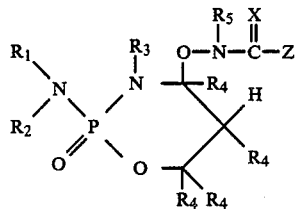

wherein X is oxygen or sulfur, $R_1$, $R_2$, and $R_3$ can be the same or different and represent hydrogen, methyl, ethyl, 2-chloroethyl or 2-methanesulfonyloxyethyl, the residues $R_4$ can be the same or different and represent hydrogen, methyl or ethyl, $R_5$ is hydrogen, $C_{1-4}$-alkyl, hydroxy-$C_{1-4}$-alkyl or phenyl and Z among others also is a $C_1$–$C_{18}$-alkylamino group, which can contain different substituents, among others the carboxy group and their pharmaceutically usable salts. In this German OS there is described as example a compound wherein Z is the group —NH—$CH_2$—COOH and the corresponding cyclohexylamine salt.

The compounds of Belgian Pat. No. 892589 and German published application No. 3133309 possess antitumor action as well as an immunosuppresive action.

SUMMARY OF THE INVENTION

The present invention is directed to the salts of oxazaphosphorine derivatives of the formula

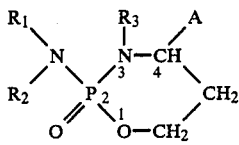

where $R_1$, $R_2$, and $R_3$ are the same or different and represent hydrogen, methyl, ethyl, 2-chloroethyl, or 2-methanesulfonyloxyethyl and wherein at least two of these residues are 2-chloroethyl and/or 2-methanesulfonyl-oxyethyl and A is the group —S—alk—$SO_3H$ or —N(OH)—CONH—alk—$CO_2H$ and alk represents a $C_2$–$C_6$-alkylene residue optionally containing a mercapto group, whereby alk also can be —$CH_2$— in case there is a carboxy group attached to the alk group, with homocysteinethiolactone or α-amino-ε-caprolactam or a basic compound of the formula:

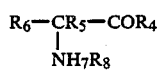

wherein $R_4$ is a hydroxy group, an amino group or a $C_1$–$C_6$-alkoxy group, $R_5$ is hydrogen or a difluoromethyl group, $R_6$ is hydrogen, an indolyl-(3)-methyl residue, imidazolyl-(4)-methyl residue, a $C_1$–$C_{10}$-alkyl group or a $C_1$–$C_{10}$-alkyl group which is substituted by a hydroxy group, a $C_1$–$C_6$-alkoxy group, a mercapto group, a $C_1$–$C_6$-alkylmercapto group, a phenyl group, a hydroxy phenyl group, an amino-$C_1$–$C_6$-alkylmercapto group, an amino-$C_1$–$C_6$-alkoxy group, an amino group, an aminocarbonyl group, a ureido group ($H_2NCONH$—), a guanidino group or a $C_1$–$C_6$-alkoxycarbonyl group, or wherein $R_6$ together with the structured portion $>CR_5(NR_7R_8)$ forms the proline residue, the 4-hydroxy-proline residue or the 2-oxo-3-amino-3-difluoromethyl-piperidine and the residues $R_7$ and $R_8$ represent hydrogen or $C_1$–$C_6$-alkyl residues.

It also includes a process for the production of salts of oxazaphosphorine derivatives of the general formula:

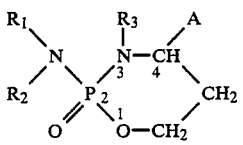

where $R_1$, $R_2$, and $R_3$ are the same or different and represent hydrogen, methyl, ethyl, 2-chloroethyl, or 3-methanesulfonyloxyethyl and wherein at least two of these residues are 2-chloroethyl and/or 2-methanesulfonyloxyethyl and A is the group —S—alk—$SO_3H$ or —N(OH)—CONH—alk—$CO_2H$ and alk represents a $C_2$–$C_6$-alkylene residue optionally containing a mercapto group, whereby alk also can be —$CH_2$— in case there is a carboxy group attached to the alk group with homocysteinethiolactone or α-amino-ε-caprolactam or a basic compound of the formula:

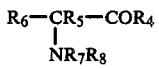

wherein $R_4$ is a hydroxy group, an amino group or a $C_1$-$C_6$-alkoxy group, $R_5$ is hydrogen or a difluoromethyl group, $R_6$ is hydrogen, an indolyl-(3)-methyl residue, imidazolyl-(4)-methyl residue, a $C_1$-$C_{10}$-alkyl group or a $C_1$-$C_{10}$-alkyl group which is substituted by a hydroxy group, a $C_1$-$C_6$-alkoxy group, a mercapto group, a $C_1$-$C_6$-alkylmercapto group, a phenyl group, a hydroxy phenyl group, an amino-$C_1$-$C_6$-alkylmercapto group, an amino-$C_1$-$C_6$-alkoxy group, an amino group, an aminocarbonyl group, a ureido group ($H_2NCONH-$), a guanidino group or a $C_1$-$C_6$-alkoxycarbonyl group, or wherein $R_6$ together with the structured portion $>CR_5(NR_7R_8)$ forms the proline residue, the 4-hydroxy-proline residue or the 2-oxo-3-amino-3-difluoromethyl-piperidine and the residues $R_7$ and $R_8$ represent hydrogen or $C_1$-$C_6$-alkyl residues characterized in that:

(a) a compound of the formula

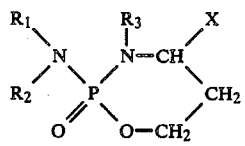

wherein X is a hydroxy group or a $C_1$-$C_4$-alkoxy group, is reacted with a salt of the compound

AH      IV wherein A has the stated meanings and the basic salt component is homocysteinethiolactone, α-amino-ε-caprolactam or the basic compound of formula II with the stated definitions for the residues $R_4$ to $R_8$ or first is reacted with the compound AH and subsequently with the previously mentioned basic compounds or a compound of the formula III wherein X is benzylthio, $C_1$-$C_6$-alkanoylthio, $C_1$-$C_{10}$-alkylthio, $C_1$-$C_{10}$-alkylthio substituted by a carboxy group, a hydroxy group or a $C_1$-$C_4$-carbalkoxy group or wherein X is the group —N(OH)—CO—NHR and R is hydrogen, $C_1$-$C_6$-alkyl, benzyl, phenyl, halogene-phenyl or alkylphenyl or wherein X is the group A and X can also exist in the salt form, is reacted with the excess of the compound of the formula

A'H      V or a salt of the compound A'H or with homocysteinethiolactone, α-amino-ε-caprolactam or the basic compound of formula II with the stated meanings for the residues $R_4$ to $R_8$, wherein A' is different from A and has the definitions stated for A or (b) a compound of the formula I or the salt of compound of general formula I is reacted with homocysteinethiolactone, α-amino-ε-caprolactam or a basic compound of formula II with the stated definitions for $R_4$ to $R_8$ with formation of the corresponding salt and optionally the basic components in the compounds formed or the acid hydrogen of the group A in case A is not in the salt form are exchanged for another basic component within the scope of the definitions given for these substituents.

Also there is included in the invention drugs containing such salts together with carriers and/or diluents and/or adjuvants. Additionally there are included such drug compositions which additionally include a buffer and/or the alkali salt of a mercapto-$C_2$-$C_6$-alkanesulfonic acid.

The drugs can be prepared by processing a compound of formula I with customary pharmaceutical carriers or diluents or other adjuvants to form pharmaceutical preparations or can be brought into a therapeutically usable form. In such processing there can also be included a buffer and/or the alkali salt of a mercapto-$C_2$-$C_6$-alkanesulfonic acid.

In the above formulae I and II the $C_1$-$C_6$-alkoxy group for example can be methoxy, ethoxy, propoxy, isopropoxy, butoxy, hexoxy, the $C_1$-$C_{10}$-alkyl group for example can be methyl, ethyl, propyl, isopropyl, butyl, sec.butyl, hexyl, octyl, or decyl, the $C_1$-$C_6$-alkylmercapto group for example can be methylmercapto, ethylmercapto, butylmercapto, or hexylmercapto, the amino-$C_2$-$C_6$-alkyl group for example can be aminomethylmercapto, aminoethylmercapto, aminobutylmercapto, aminohexylmercapto, the amino-$C_1$-$C_6$-alkyloxy group for example can be aminomethoxy, aminoethoxy, aminobutoxy, or aminohexoxy.

The compounds of the invention possess a strong antitumor activity and can be used especially to combat cancer. Compared to the known compounds of Belgian Pat. No. 892589 and German published application No. 3133309 they have, for example, a reduced toxicity (for example reduced acute toxicity and leucotoxic action) and therefore have an improved therapeutic index and a better local and systemic as well as venous compatibility. Furthermore, the compounds of the invention possess a reduced immunosuppressive action, a reduced local tissue irritation and frequently lower haemolytic action. Furthermore, the compounds of the invention do not have or only have slight circulatory side effects (for example, sympathetic actions). Also the blood pressure is less disturbingly influenced.

The alkylene residue (alk) of formula I can be straight or branched. Examples of these are methylene, dimethylene, trimethylene, tetramethylene, pentamethylene or hexamethylene residues or also for example the residues

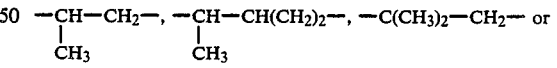

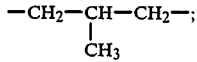

the chain especially consists of 2 or 3 carbon atoms when it is unbranched. In the event alk is branched the portion which is attached to the acid group and the sulfur or nitrogen atom especially consists of 2 to 3 carbon atoms. In the event the carboxy group is on the group alk then alk is preferably —$CH_2$—. In the event the residue alk contains a mercapto group (this can especially be the case when it is a matter of the group —S—alk—$SO_3H$), this mercapto group can be on the 1-, 2-, 3-, 4-, or 5-positioned carbon atom. The numbering begins with the carbon atom on which there is the acid group, for example, the —$SO_3H$ group. Especially thereby it is a matter of the —$CH_2$—CH(SH)—$CH_2$— group.

Preferably there are employed compounds where $R_3$ is hydrogen, $R_1$, and $R_2$ are 2-chloroethyl in each case and A is the group —S—$CH_2$—$CH_2$—$SO_3H$ or —N(OH)—CO—NH—$CH_2$—$CO_2H$.

The alkyl groups, alkoxy groups, and alkylmercapto groups occurring in formula II can be straight or branched. The $C_1$-$C_{10}$-alkyl group preferably contains 1-6 carbon atoms. With the alkoxy groups and the alkylmercapto groups it is a matter of preferably those containing 1-4, especially 1-2, carbon atoms; the same is true in regard to the residues $R_7$ and $R_8$ and even these are alkyl residues. In the event $R_6$ in formula II is an alkyl group which contains an amino-$C_1$-$C_6$-alkylmercapto ($C_1$-$C_6$-alkoxy) group then it is a matter of preferably the following groups: $H_2N$—$CH_2$—$CH_2$—S—$CH_2$— or $H_2N$—$CH_2$—$CH_2$—O—$CH_2$—.

With the compounds of formula II it is a matter of preferably those compounds where $R_4$ is a hydroxy group and the residues $R_5$, $R_7$, and $R_8$ are hydrogen and $R_6$ especially takes on the meanings which are given below:

Preferred basic compounds of formula II are for example those where $R_4$ is a hydroxy group, $R_5$ is hydrogen or difluoromethyl, $R_6$ is a $C_1$-$C_{10}$-alkyl group, especially the $C_1$-$C_6$-alkyl group which contains (preferably in the 2-, 3-, 4-, 5-, or 6-position; numbering always beginning on the linkage point of the alkyl group with the rest of the molecule), an amino group (especially in the 3- or 4-position), an amino-$C_2$-$C_4$-alkylthio group, an amino-$C_2$-$C_4$-alkoxy group, a guanidino residue, an imidazolyl-(4)-methyl residue or an indolyl-(3)-methyl residue and $R_7$ and $R_8$ are hydrogen or a $C_1$-$C_4$-alkyl residue; or aminoacid derivatives of formula II where $R_4$ is an amino group or a $C_1$-$C_4$-alkoxy group, $R_5$ is hydrogen, $R_6$ is hydrogen, a phenylmethyl group, a 4-hydroxyphenylmethyl group or a $C_1$-$C_6$-alkyl group which contains (preferably in the 2-, 3-, 4-, 5-, or 6-position) a hydroxy group, a mercapto group, a $C_1$-$C_4$-alkylmercapto group, an aminocarbonyl group, a $C_1$-$C_4$-alkoxycarbonyl group or a ureido group and $R_7$ and $R_8$ are hydrogen or a $C_1$-$C_4$-alkyl residue.

In the previously mentioned aminoacids or aminoacid derivatives the salts for example are formed in each case from one mole of oxazaphosphorine I and one mole of the compound II.

Furthermore, there can be used as basic compounds of formula II for example those compounds where $R_4$ is an amino group or a $C_1$-$C_4$-alkoxy group, $R_5$ is hydrogen or difluoromethyl, $R_6$ is a $C_1$-$C_{10}$-alkyl group, especially a $C_1$-$C_6$-alkyl group which contains (preferably in the 2-, 3-, 4-, or $\omega$-position) an amino group, an amino-$C_2$-$C_4$-alkylthio group, an amino-$C_2$-$C_4$-alkoxy group, a guanidino residue, an imidazolyl-(4)-methyl residue or an indolyl-(3)-methyl residue and $R_7$ and $R_8$ are hydrogen or a $C_1$-$C_4$-alkyl residue.

In the last mentioned aminoacid derivatives the salts are formed for example in each case from 2 moles of oxazaphosphorine and 1 mole of the aminoacid derivative of formula II.

Specific examples of compounds of formula II are:

aspartic acid diamide (DL-form), diethyl ester of aspartic acid (L-form), citrullinamide ($H_2N$—CO—NH—$(CH_2)_3$—CH($NH_2$)—$CONH_2$, L-form), ornithine ethyl ester (L-form), arginine, arginiamide (L-form), 4-thialysine ($H_2N$—$CH_2$—$CH_2$—S—$CH_2$—CH($NH_2$)—COOH), 2,6-diamino enanthic acid ($\epsilon$-methyl lysine), 4-oxalysine ($H_2N$—$CH_2CH_2$—O—$CH_2$—CH($NH_2$)—COOH), glycinamide, N,N-dimethyl glycinamide as well as the corresponding methyl or ethyl ester, prolinamide, hydroxylprolinamide, phenylalanin-amide, the methyl or ethyl ester of alanine or of phenylanine, homocysteinethiolactone (DL-form), $\alpha$-amino-$\epsilon$-caprolactam (D(+)-form), lysine (especially L-lysine), difluoromethyl-ornithine (DL- or L-form), methyl ester of valine (L-form), ethyl ester of threonine, methyl ester of histidine, histidinamide, alaninamide and ornithine.

In the salts of the invention in the event in compound II $R_4$ is an amino group or an alkoxy group and otherwise no basic group is present or in the case where $R_4$ is the hydroxy group and otherwise a basic group is present, compound I (acid-component) and Compound II (basic component) are present practically in the ratio 1:1. (This is also true in the event the basic component is homocysteinethiolactone or $\alpha$-amino-$\epsilon$-caprolactam.) On the other hand if in the basic component II $R_4$ is an amino group or an alkoxy group and this contains besides the $\alpha$-amino group an additional basic group then generally the ratio of compound I to compound II is 2:1. The salts of the invention are neutral salts. In the case of the sulfonic acid salts the pH for example is between 3.5 and 6. In the case of the carboxylic acid the pH for example is between 6-9, especially 6-8.

In regard to Process (a):

The process is carried out in a solvent at temperatures between $-60°$ C. and $+90°$ C., preferably $-30°$ C. to $+60°$ C., especially $-20°$ to $+30°$ C., that is in a given case with cooling, at room temperature or with heating. The reaction can be carried out in the presence of an acid catalyst, such as an inorganic or organic acid such as for example trichloroacetic acid, p-toluenesulfonic acid, trifluoromethanesulfonic acid or even a Lewis acid such as $AlCl_3$, $ZnCl_2$, $TiCl_4$ or boron trifluoride etherate. The pH is adjusted to between 1 and 8, preferably between 2 and 6 for the reaction. This is especially true if the starting compounds are employed in form of the salts, optionally also if the free acids are employed and A contains the carboxy group.

As solvents there can be considered for example: water, alcohols, especially alkanols having 1-6 carbon atoms such as methanol, ethanol, propanol or isobutanol, hexanol, alkyl ketones containing 1-4 carbon atoms in the alkyl groups such as especially acetone or methyl ethyl ketone, also diethyl ketone, methyl butyl ketone, aprotic solvents (for example dimethyl sulfoxide, acetonitrile, N-methyl pyrrolidine, dimethyl formamide, hexamethylphosphoric acid triamide), halogenated hydrocarbons having 1-3 carbon atoms such as chloroform, ethylene dichloride and propylene dichloride, saturated cyclic ethers such as tetrahydrofuran, dioxane, saturated lower aliphatic ethers such as diethyl ether or similar solvents, respectively mixtures of several of such solvents.

In case in starting compound III the symbol X is the hydroxy or alkoxy group, the reaction can also be carried out in 2 steps, for example, by first reacting compound III with compound AH (without acidification) and subsequently adding to the reaction mixture, optionally after concentration and addition of another of the solvents, mentioned, the basic component II or homocysteine-thiolactone or $\alpha$-amino-$\epsilon$-caprolactam in a solvent.

The use of a compound III wherein X is the hydroxy group or an alkoxy group, is especially suited in case the end product is obtained in crystalline form.

In the event that X is not hydroxy or alkoxy or X is in salt form, the compound A'H or compound A'H in salt form is employed in excess, for example, 1.5-10 molar, preferably 2-5 moles of the compound A'H or the salt of A'H per mole of compound III. The pH of the reaction solution is adjusted for example to 5.5-9, preferably 6.5-8 by means of alkali solution, e.g. aqueous sodium hydroxide,, or with the amine which is already present as the basic component in the salt employed,, under certain circumstances a pH up to 12 can also be favorable especially if the starting compounds are employed in salt form or in form of the free acids (for example if A contains the carboxy group). The reaction temperature for example is 10°-90° C., preferably 25°-60° C. The reaction time for example is several seconds to several hours. Subsequently for example the reaction solution is cooled to below 10° C. and brought to a pH between 4 to 5.5 or optionally to pH 7 with a mineral acid ($H_2SO_4$, HCl, phosphoric acid), a sulfonic acid (for example mercapto-$C_1$-$C_6$-alkanesulfonic acids, e.g. mercaptomethanesulfonic acid or mercaptohexanesulfonic acid, or an ion exchanger ($H^+$) form).

The isolation of the product of the process for example can be carried out: by crystallization or by a chromatographic process, especially by preparative high pressure liquid chromatography, optionally once again with subsequent reaction in the desired salt form on a correspondingly loaded cation exchanger.

In the event that the group A of formula III is present in salt form for example, there can be employed salts such as those described in German Offenlegungschrift No. 3133309 or Belgian Pat. No. 892589, the entire disclosure of which are hereby incorporated by reference. For example there can be used the ammonium salt, the cyclohexylammonium salt or the guanidinium salt. It goes without saying that other customary salts can also be employed, for example, customary optical bases used for resolution of a racemate, which salts are producible in a manner analogous to the methods described there.

Starting compounds of formula III for example are also described in the following references or may be produced in a manner analogous to the methods described there: Tetrahedron Letters Nr. 10 (1979), pages 883-886, Cancer Treatment Reports 60, Nr. 4 (1976), pages 429-435. If X is an optionally substituted $C_1$-$C_{10}$-alkylthio group especially compounds of formula III are used wherein X has the following meanings: $C_1$-$C_6$-alkylthio, the group —S—$(CH_2)_n$—$CO_2H$ (n=1-6, especially 1-3), the group —S—$(CH_2)_n$—OH (n=2-6, especially 2-4) or the group —S—$(CH_2)_n$—$COOC_2H_5$ (n=1-6, especially 1-3). If X is a $C_1$-$C_6$-alkanoylthio-group preferably acetylthio is used. If X is the group —N(OH)—CO—NHR and R is $C_1$-$C_6$-alkyl preferably R consists of 1-4 especially 1-2 carbon atoms.

The production of the starting salts AH of formula IV, respectively the starting salts A'H of formula V can be carried out for example by reaction of a compound AH or A'H with a basic compound or homocysteinethiolactone or α-amino-ε-caprolactam or a compound of formula II with or without a solvent at temperatures between 0° and 40° C. As solvents there can be used for example water, $C_1$-$C_6$-alkanols (methanol, ethanol), lower aliphatic ketones (acetone), cyclic ethers (dioxane), chlorinated hydrocarbon (methylene chloride, ethylene dichloride, chloroform, carbon tetrachloride), saturated lower aliphatic ethers (diethyl ether), aprotic solvents (for example dimethylformamide, dimethylsulfoxide, acetonitrile) or mixtures of these agents.

The production of this type of salt also can be carried out for example in such manner that an alkali salt (sodium salt) of the acid AH respectively A'H is dissolved in water (for example 1 to 20% solution; %=weight percent), this solution allowed to run through a column containing a strongly acid ion exchanger ($H^+$ form, 3 fold excess) and the free acid in the eluate is neutralized with the basic component, the mixture concentrated in a vacuum, and optionally the residue recrystallized with a lower alcohol (methanol, ethanol), a lower ketone (acetone) or an ether (diethyl ether).

In Regard to Process (b):

This process is carried out at temperatures between 0°-25° C., preferably 0°-5° C. As solvents for this process there can be used for example: water, lower aliphatic alcohols, lower aliphatic ketones or mixtures of these agents, there is reacted 1 mole of component I with 1 mole of component II. It is suitable to operate in a pH range between 3 and 8. In using compounds I wherein A is the S—alk—$SO_3H$ group (or a salt thereof) preferably there is employed a pH between 3-6, preferably 3.8-5, especially pH 4; in using compounds I wherein A is the —N(OH)—CO—NH—alk-—$CO_2H$ (or a salt thereof) there is preferably employed a pH between 6-8, preferably pH 7.

Frequently the addition of a buffer is favorable. As buffer systems with a pH range between 3.8 to 5.0 for example, there can be used: citric acid/sodium citrate; acetic acid/sodium acetate; phosphoric acid/sodium hydrogen phosphate; tartaric acid/sodium tartrate; aminoacid/sodium formate; sodium hydrogen phosphate/citric acid; succinic acid/sodium succinate; propionic acid/sodium propionate; aconitic acid/sodium aconitate; β,β-dimethylglutaric acid and its sodium salt; maleic acid/sodium maleate; compound II/citric acid. As buffer for a pH range of 6 to 8 there can be used for example: sodium citrate/NaOH, tris(hydroxymethyl)-aminomethane-maleate/NaOH, $KH_2PO_4$/NaOH, $KH_2PO_4$/$Na_2HPO_4$.

Instead of sodium hydroxide solution to produce the buffer there can also be used homocysteinethiolactone or α-amino-ε-caprolactam or a basic compound of formula II so that the buffer already contains the basic component, which also is present in the end product of formula I.

The exchange of the basic component of a salt of compound I against a basic component of the invention can be carried out for example on acid ion exchangers which are loaded with homocysteinethiolactone, α-amino-ε-caprolactam or the basic compound of formula II. In this case the basic compound II (which now is bound on the acid groups of the ion exchanger) is employed in excess (for example 2 to 10 moles, perferably 5 moles of component II to 1 mole of component I). As acid ion exchangers there can be used for example those whose polymeric matrix carry sulfonic acid groups or carboxylic acid groups. The matrix of the ion exchanger for example can consist of a polystyrene resin optionally containing 2 to 16%, preferably 4 to 8% of divinyl benzene or a phenol resin, e.g. phenolformaldehyde. The polystyrene ion exchanger is preferably in gel form. The loading of the ion exchanger with the basic components for example can be carried out in the following manner: 150 ml of ion exchange resin, 1.2 mval/ml (the producer of the ion exchanger states the capacity of the ion exchanger (that is the amount of functional groups such as —SO$_3$H, —CO$_2$H) in mval/ml or mval/g) of the ion exchanger resin in a column (diameter about 4 cm) with a cooling jacket is regenerated with hydrochloric acid, washed with distilled water until neutral and free of chloride ions. Subsequently the ion exchanger is treated with a 10% aqueous solution of the basic compound (220 mmoles) and washed with distilled water. Additionally, the ion exchanger can be treated with a buffer (citric acid/citrate or acetic acid/acetate) of pH about 4 and subsequently the buffer again washed out. Furthermore, the ion exchanger also can be loaded with neutral aminoacid salts of formula II or neutral salts of homocysteinethiolactone or α-amino-ε-caprolactam (for example the hydrochloride or hydrobromide).

In the event an ion exchanger is used it is favorable to add the buffer in the receiver for the eluate. In a few cases the common elution of the salt with the buffer and/or the salt of a mercapto-C$_2$-C$_6$-alkanesulfonic acid through the ion exchanger is also advantageous. For example, the starting compound, that is the compound I (A=S—alk—SO$_3$H) or a customary known salt of compound I is dissolved in a buffer at pH 3.8 to 5.0, preferably 4.1 and this solution is passed over the ion exchange column and the eluate is caught in a corresponding buffer solution. The eluate or the lyophilizate produced therefrom then consists of the salt according to the invention and the buffer and/or the salt of the mercaptoalkanesulfonic acid. Preferably the eluate, in a given case after dilution with water, is immediately frozen or lyophilized in some cases. In the event in the starting compound I the symbol A is the group —N(OH-)—CO—NH—alk—CO$_2$H, an analogous procedure is used but then the pH is between 6-8 (for example pH 7).

However, hereby the procedure can also be that a customary salt of compound I (for example an alkali salt) in aqueous solution is allowed to run through an acid ion exchanger as mentioned above in the H$^+$ form and the compound I then neutralized in the eluate with the basic component of formula II or with homocysteinethiolactone or α-amino-ε-caprolactam. This optional way of proceeding is especially suitable if the end product is produced in crystalline form.

As starting salts of the compound of formula I there can be used for example those which are described in German Offenlegungschrift No. 3133309 or Belgian Pat. No. 892589. For example, there can be used the ammonium salt, the cyclohexylammonium salt or the guanidinium salt. However, there can also be employed other customary salts (for example salts with optically active bases which are customary for resolution of a racemate), which are producible in a manner analogous to the methods described there.

Included in the oxazaphosphorine derivatives of formula are all possible stereoisomers and mixtures thereof. In detail for example it is a matter of cis-trans isomers on the oxazaphosphorine ring, that is cis-or-trans-position of the group A to the oxo-atom in the 2-position (phosphoryl oxygen). Thus for example, it is a matter of the cis isomers and the trans isomers (at times the racemate and the corresponding enantiomers), the separated cis isomers and the separated trans isomers. Diastereomer salts (for example if a chiral amine is used for salt formation), can be separated in known manner, preferably through fractional crystallization. The pure enantiomers can be obtained according to the customary methods of resolving racemates, for example through fractional crystallization of the diastereomer salts from racemic acids of formula I and optically active bases or in a given case, through use of optically active starting materials according to formula III in the synthesis.

Generally in the synthesis cis/tran mixtures can be formed. Generally, mixtures are formed which consist of preponderantly the cis isomers and up to about 5–10% of the trans isomers. For example, the compounds according to Examples 1–5 consist of the cis isomers with less than 5–10% of the trans form.

With good crystallizing compounds there are obtained from such mixtures the crystallized cis or the trans form, especially the cis-form. However, if the reaction is carried out in water free solvents or in solvents with a slight portion of water, there is obtained exclusively or in wide preponderance a single form, especially the cis-form. Thus there can be produced for example the pure cis-form of a noncrystallizing or poorly crystallizing compound of formula I by adding an acetonic solution of the compound of formula III to an aqueous solution of the compound of formula IV or its salt at temperatures between −30° and +20° C. and after the end of the reaction precipitating several times.

The starting compounds of formula III can be employed as racemic cis and trans isomers (production of which are shown above), as optically active cis and trans forms and as mixtures thereof (in this connection see Belgian Pat. No. 892589 and German Offenlegungschrift No. 3133309, page 12).

For resolution of the racemate there can be employed for example as optically active bases 1-phenylethylamine, brucine, quinidine, strychnine and cinchonine as well as additional bases and methods which are described in "Optical Resolution Procedures for Chemical Compounds", volume 2, Paul Newman, 1981, Publisher Optical Resolution Information Center in Riverdale, USA. For this purpose for example a racemic salt of the invention is converted into a salt with one of the previously mentioned optically active bases in the manner already stated, the enantiomers separated in known manner and then the optically active base of the thus obtained enantiomers replaced again by a basic compound according to the invention. However, the precedingly mentioned optically active bases can also be employed in the synthesis in process (a) in the reaction of a compound of formula III with a compound of formula IV or V or in process (b) as basic salt component. In this case this optically active base subsequently is exchanged in customary manner against the basic salt component of the invention corresponding to the already given definition.

The basic salt components of the invention homocysteinethiolactone, α-amino-ε-caprolactam as well as the compounds of formula II can be employed as the racemate or in the form of the pure enantiomers.

Generally the L-forms are preferred.

Included in the salts of the invention are all forms which result from the presence of various asymmetric carbon atoms, thus for example, racemates, optically active forms, diastereomer forms.

It is recommended in producing the salts of the invention to hold them in solution for as short a time as possible in order to prevent the hydrolysis to 4-hydroxyoxazaphosphorines and/or epimerization of the oxazaphosphorine ring (conversion of the cis-form into the trans-form) or to hold the hydrolysis as low as possible. In the event that the salts of the invention are strongly contaminated (for example contain large amounts of starting compounds), they can be obtained in pure form through customary chromatographic methods or preparative high pressure liquid chromatography.

The salts of the invention are stable, have storage stability (especially at 4° C.), and can be readily galenically worked up. For galenic preparations (for example hydrolysis stable injection solutions, lyophilizates), especially in regard to storage stability it is also recommended to establish a pH range of about 3.5–7 with the sulfonic acid derivatives with the help of customary buffers (for example citrate buffer). The optimum pH hereby is 4.0–4.3. In the event that the residue A is derived from the group N—(OH)—CO—NH—alk-—CO$_2$H, suitably a pH of 6.5–7.5 is established. These pH adjustments can be carried out both for solutions and suspensions and also for solid galenic preparation.

Furthermore and independent of the addition of a buffer the addition of 0.5 to 5 equivalents of a salt (for example alkali salt, especially the sodium salt) of a mercapto$_2$-C$_6$-alkylsulfonic acid (for example a salt of 2-mercapto-ethane-sulfonic acid) and its disulfide and further thiols (for example cysteine) is also advantageously. Types of thiols and disulfides and the methods of their use are described in European patent application No. 83439 and corresponding Hohorst U.S. application Ser. No. 454,865, filed Dec. 30, 1982, the entire disclosure of which is hereby incorporated by reference. As this kind of salt there can be used for example the alkali salts (Na, K) or the salts with a basic component according to the invention (compound of formula II, homocysteinethiolactone, α-amino-ε-caprolactam).

The addition of the salt of mercapto-C$_2$–C$_6$-alkanesulfonic acid for example can be carried out by addition of an aqueous solution of the salt of the sulfonic acid (alkali salt, for example 20 weight percent) to an aqueous solution of the salt of the invention (preferably buffered to a pH between 4 and 4.3). The thus obtained mixture then for example is lyophilized.

The advantages in addition of a mercaptoalkanesulfonic acid salt by this means consist of the following: improvement of the storage stability as well as of the stability in aqueous solution with the salts of the invention. (For example this is of significance in the production of the salts and also is useful for example in solution of lyophilizates before use); improvement in chemotherapy of cancer illnesses by means of the salts of the invention, especially in regard to toxic side effects (cf. European patent application No. 83439 and the corresponding Hohorst U.S. application Ser. No. 454,865 and European Pat. No. 2495.

The salts of the invention are suitable for the production of pharmaceutical compositions or preparations. The pharmaceutical compositions or drugs contain one or more of the salts of the invention as active material, optionally in admixture with other pharmacologically or pharmaceutically active materials. The production of the drugs can be carried out using known and customary pharmaceutical carriers and adjuvants.

The drugs for example can be used enterally, parenterally, orally, perlingually or in the form of sprays. Dispensing can be carried out for example in the form of tablets, capsules, pills, dragees, plugs, liquids, or aerosols. As liquids there can be used for example: oily or aqueous solutions or suspensions, emulsions injectable aqueous or oily solutions or suspensions.

The compounds of the invention show a good cytostatic and curative effect in intraveneous, intraperitoneal or oral application with various experimental tumors of the rat and the mouse. For example there was produced, depending the dosage, a curative effect with the compounds of the invention on the rat 5 days after intraperitoneal implantation of 10$^5$ cells of luekemia L5222 with different doses applied intravenously, intraperitoneally or orally. As healing there is defined the recidive and metastasis free survival of tumor carrying animals after 90 days. From the frequency of healing obtained with the different dosages by means of test analysis according to R. Fisher there was calculated as average curative dosage (DC 50) that dosage with which there could be healed 50% of the tumor carrying animals.

For example, the compounds of the invention were also dispensed at various doses intravenously, intraperitoneally, or orally one day after intraperitoneal implantation of 10$^6$ cells of the Yoshida-Ascites-Sarcoma AH 13 had a curative effect produced depending on the dosage.

Here also the curative effect was defined as recidive and metastasis free survival of the tumor carrying animals for 90 days.

In corresponding manner by means of test analysis according to R. Fisher there was calculated as the average curative dosages (DC 50) that dosage at which 50% of the tumor carrying animals could be healed.

Furthermore, for example, the compounds of the invention were dispensed with various doses intravenously, intraperitoneally, or orally once or multiple times (4×) on successive days after intraperitoneal implantation of 10$^6$ cells of the mouse leukemia L1210 and a cytostatic effect produced.

The cytostatic effect is conceived as increase of the median survival time of the tumor bearing animals and is expressed as dosage dependent percent increase of the survival time compared to an untreated control group.

The average curative dosage with the rat tumors is independent of the form of dispensation in the range of 0.1–10 mg/kg. With the same doses there is produced an increase of the median survival time of 100% with the mouse leukemia L1210.

Furthermore, the compounds of the invention stimulate the production of antibodies in a specific lower dosage range. This dosage range for example for the compound according to Example 5 is between 20–50 mg/kg rat (intravenously, intraperitoneally). In comparison in the same dosage range the antibody production of the known antitumor agent cyclophosphamide is already suppressed.

Literature:

N. Brock: Pharmakologische Grundlagen der Krebs Chemotherapie

In: A Georgii (Hrsg), Verhandlungen der Deutschen Krebsgesellschaft Volume 1, pages 15–42, Gustav Fischer Verlag, Stuttgart (1978)

This curative and cytostatic effect is comparable with the effect of the known medicines cyclophosphamide and ifosfamide.

The lowest curative or cytostatically effective dosage in the stated animal experiment for example is:

0.01 mg/kg orally
0.01 mg/kg introperitoneally
0.01 mg/kg intravenously

As general dosage range for the curative and cytostatic action (animal experiments as above) there can be considered:

0.01–100 mg/kg orally, especially 0.1–10.0 mg/kg 0.01–100 mg/kg intraperitoneally, especially 0.1–10.0 mg/kg 0.01–100 mg/kg intravenously, especially 0.1–10.0 mg/kg The compounds of the invention are indicated for use in malignant illnesses of animals.

The pharmaceutical preparations generally contain between 1 mg and 1 g, preferably 100 to 1000 mg of the active component (or components) of the invention.

The dispensation can be carried out for example in the form of tablets, capsules, pills, dragees, plugs, salves, gels, creams, powders, dusts, aerosols, or in liquid form. As liquid forms of use there can be employed for example: oily or alcoholic or aqueous solutions as well as suspensions and emulsions. Preferred forms of use are tablets which contain between 10 and 200 mg or solutions which contain between 0.1 to 5% active materials.

The individual dosage of the active components according to the invention for example can be (a) with oral forms of the medicine between 1–100 mg/kg, perferably 10–60 mg/kg, (b) with parenteral forms of the medicine (for example intravenously, intramuscularly) between 1–100 mg/kg, perferably 10–60 mg/kg, (c) with forms of the medicine for application rectally or vaginally between 1–100 mg/kg, preferably 10–60 mg/kg, (d) with forms of the medicine for local application to the skin and mucous membranes (for example in the form of solution, lotions, emulsions, salves, etc.) between 1–100 mg/kg, preferably 10–60 mg/kg.

The doses in each case are based on the free base.

For example there can be recommended 1–3 times daily 1 to 10 tablets having an active material content of 10 to 300 mg or for example with intravenous injection 1 to 2 times daily one or more ampoules containing 1 to 10 ml containing 10 to 250 mg of material. The minimum daily dosage with oral dispensation for example is 200 mg; the maximum daily dosage with oral dispensation should not exceed 5000 mg.

There can also be recommended in individual cases dosages over 12 and more hours corresponding to a continuous infusion.

The individual dosage in treating dogs and cats orally generally is between about 10 and 60 mg/kg body weight; the parenteral dosage is between about 10 and 60 mg/kg body weight.

The individual dosage in treating horses and cattle orally generally is between about 10 and 60 mg/kg body weight; the parenteral individual dosage is between about 10 and 60 mg/kg body weight.

The acute toxicity of the compounds of the invention on the mouse/expressed by the LD 50 mg/kg; method according to Miller and Tainter; Proc. Soc. Exper. Biol. a Med. 57 (1944)261) for example with oral application is between 100 and 1000 mg/kg (or above 1000 mg/kg).

The drug can be used in veterinary medicine as well as in agriculture alone or in admixture with other pharmacologically active materials.

The compositions can comprise, consist essentially of, or consist of the stated materials and the process can comprise, consist essentially of, or consist of the recited steps with such materials.

Unless otherwise indicated all parts are by weight.

DETAILED DESCRIPTION

Example 1

4-(2-Sulfo-ethylthio)-Cyclophosphamide-Glycinamide Salt (Cyclophosphamide is 2-[2-(bis-(2-chloroethyl)-amino)]-2-oxo-tetrahydro-2H-1,3,2-oxazaphosphorine)

4.0 grams (18 mmoles) of 4-hydroxycyclophosphamide in 10 ml of distilled water were treated with 5 grams (18 mmoles) of 2-mercaptoethanesulfonic acid-glycinamide salt in 40 ml of acetone. The reaction solution was acidified with trichloroacetic acid to a pH of 4, kept for 2 hours at 5° C. and for 20 hours at −25° C. The salt separated out in crystalline form and was filtered off with suction, washed, dried, and recrystallized from water/acetone. M.P. 90°–98° C.; Yield 7.2 grams (76% of theory). The salt contains about 1 equivalent of acetone.

Example 2

4-[1-Hydroxy-3-carboxymethyl-ureido-(1)]cyclophosphamide-Lysine salt (L-Lysine)

7.5 grams (24.6 mmoles) of 4-ethoxycyclophosphamide and 3 grams (22.4 mmoles) of 1-hydroxy-3-carboxymethyl-urea were kept in 50 ml of dry alcohol for 20 hours at 0° C. Subsequently the reaction solution was concentrated at 20° C. in a vacuum, the residue taken up in 200 ml of acetone, treated with 3.3 grams (22.6 mmoles) of L-lysine in 25 ml of methanol and the gelatinous precipitate centrifuged after standing for a short time. The residue was dissolved in water, filtered, precipitated with acetone, filtered off with suction and washed with acetone) ether. M.P. 125°–128° C.; Yield: 6.5 grams (54% of theory).

Example 3

4-(2-Sulfo-ethylthio)-cyclophosphamide-Glycinamide Salt

A solution of 3.1 grams (6.5 mmoles) of 4-(3-sulfopropylthio)-cyclophosphamide-guanidine salt and 4.2 grams (19.6 mmoles) of 2-mercaptoethanesulfonic acid-glycinamide salt in 15 ml of water was adjusted to pH 7.5 with aqueous sodium hydroxide and heated for 5 minutes at about 40° C. Subsequently the reaction solution was cooled to 0° C., adjusted to pH 4.5 with sulfuric acid, treated with 70 ml of acetone and kept for 3 days at 40° C. The precipitate filtered off with suction and recrystallized from water/acetone. M.P. from 85° C. (decomposition); Yield: 430 mg (14% of theory).

Example 4

4-(2-Sulfo-ethylthio)-Cyclophosphamide-Arginine Salt (L-Arginine) 37.2 grams (74.5 mmoles) of 4-(2-sulfoethylthio)-cyclophosphamide-cyclohexylamine salt were dissolved in 320 ml of distilled water at 5° C. (pH 4.3) and passed over a column cooled to 4° C. and containing 150 ml of cation exchanger. There was used a gel formed polystyrene resin containing 8% divinyl benzene and also containing sulfonic acid groups, which cation exchanger was loaded with arginine. Flow through velocity: 6 ml/minute. It was rinsed with 250 ml of water. The eluate cooled to 4° C. was diluted with cold water to a 5% solution and subsequently lyophilized.

M.P. 85°–90° C. (decomposition); Yield: 42.9 grams (100% of theory).

The addition of a buffer material and/or a mercaptoalkylsulfonic acid can be carried out as follows:

(a) Addition of Sodium Citrate Buffer

The procedure is as stated above but the eluate is caught in sodium citrate buffer (pH 4.1) and diluted for example subsequently to a solution which is 0.5 molar in sodium citrate and 5% in active material. Subsequently the solution was lyophilized.

Yield: 42.9 grams (100% of theory), compound of Example 4 with sodium citrate buffer.

(b) Addition of Sodium Citrate Buffer and Sodium-2-mercapto-ethanesulfonate (Mesna)

The procedure is as stated above except that the eluate is caught in a cooled sodium citrate buffer solution (pH 4.1) which contains 8.2 grams (50 mmoles) Mesna and the solution is subsequently lyophilized.

Yield: 42.9 grams (100% of theory) of compound of Example 4 with Mesna and sodium citrate buffer.

Example 5

4-(2-Sulfo-ethylthio)-Cyclophosphamide-Lysine Salt (L-Lysine)

37.3 grams (74.5 mmoles) of 4-(2-sulfo-ethylthio)-cyclophosphamide-cyclohexylamine salt were eluted in a manner analogous to Example 4 on an ion exchanger (protonated lysine form) and subsequently lyophilized.

M.P. from 85° C. (decomposition); Yield: 40.8 grams (100% of theory).

A different procedure for the example is the following:

82.4 grams (16.5 mmoles) of 4-(2-sulfo-ethylthio)-cyclophosphamide cyclohexylamine salt were dissolved in 850 ml of distilled water at 5° C. The solution was adjusted to pH 4.1 with several particles of strongly acid ion exchanger (having sulfonic acid groups) and at a dropping speed of 50 ml/minute passed over a column cooled to 4° C. and containing 800 ml of ion exchanger (the same ion exchanger as in Example 4) containing 820 mmoles of sulfonic acid-L-lysine groups. The first 180 ml of the eluate were discarded and the following eluate continuously adjusted under stirring and ice water cooling to pH 4.1 with in all about 1.5 ml of strongly acid ion exchanger (having sulfonic acid groups). The ion exchanger was rinsed with 900 ml of distilled water cooled to 0° C. Subsequently the eluate was diluted with cold water to a 5% solution and immediately lyophilized.

M.P. form 85° C.; Yield: 90 grams (100% of theory).

Compound According To Example 5 With Lysine-Citrate Buffer (Lysine + Citric Acid)

7.2 grams (14.4 mmoles) of 4-(2-sulfo-ethylthio)-cyclophosphamide-cyclohexylamine salt were dissolved in 80 ml of 0.05 molar sodium citrate buffer (pH 4.1) at 4° C. and passed over a column containing 40 ml of cation exchange resin (protonated lysine form) cooled to 4° C. It was rinsed with 80 ml of buffer solution, the eluate was filled up to 150 grams of solution and lyophilized.

Yield: 7.9 grams (100% of theory) of the compound of Example 5 with lysine-citrate buffer.

Compound According To Example 5 With 2-Mercaptoethanesulfonic Acid-Lysine Salt And Lysine-Citrate Buffer 7.2 grams (14.4 mmoles) of 4-(2-sulfo-ethylthio)-cyclophosphamide-cyclohexylamine salt and 1.5 grams (9.2 mmoles) of Mesna were dissolved in 80 ml of 0.05 molar sodium citrate buffer pH 4.1 at 4° C. and passed over a column containing 40 ml of cation exchange resin (protonated lysine form) and cooled to 4° C. It was rinsed with 50 and 30 ml of buffer solution, the cooled eluate filled up to 150 grams of solution and lyophilized.

Yield: 7.9 grams (100% of theory) of the compound of Example 5 with 2.6 grams (100% of theory) of 2-mercaptoethanesulfonic acid-lysine salt and lysine citrate buffer (pH 4.1).

Example 6

4-(2-sulfo-ethylthio)-cyclophosphamide-glycinamide salt 2,9 grams (8,6 mmoles) of 4-hydroxy-ethylthio)-cyclophosphamide and 5,6 grams (26 mmoles) of 2-mercaptoethanesulfonic acid-glycinamide salt were dissolved in 35 ml of distilled water. The pH was adjusted to 8 with glycinamide. The reaction solution was heated for about 4 minutes at about 40° C.: Subsequently the reaction solution was cooled to 0° C., adjusted to pH 4,5 with 2-mercapto-ethanesulfonic acid and 500 ml of acetone were added. Then the reaction mixture was kept several days at 4° C., the precipitate was filtered off with suction and recrystallized from water/acetone. M.P. from 85° C.; Yield 410 mg (9% of theory). The salt contains about 1 equivalent of acetone.

Examples of Pharmaceutical Preparations (a) Example For The Production Of A Lyophilizate Of 4-Sulfo-ethylthiocyclophosphamide-Lysine Salt 90 grams of 4-sulfo-ethylthiocyclophosphamide-L-lysine salt were dissolved with stirring in 1500 ml of water suitable for injection purposes and cooled to 4° C. Subsequently it was filled up to 1800 ml with water at 4° C. The pH was adjusted to about 4.2 with several particles of regenerated cation exchanger (H+ form). The above solution was subjected to a sterile filtration in known manner to produce the lyophilizate. The receiving vessel was cooled. All of the processes subsequent to the sterile filtration were carried out under aseptic conditions.

The sterile solution was filled to 2 ml in a 10 ml injection flask. The active material content was 100 mg.

The flasks were provided with sterile freeze drying stoppers and lyophilized in a freeze drying unit. Subsequently the unit was deaerated with sterile, dried nitrogen and the ampoule flasks closed in the unit. For the production of an injection solution the contents of the flasks were dissolved in 5 ml of water suitable for injection purposes.

The lyophilizate is stored at 0°–6° C. (refrigerator).

(b) Example For The Production Of A Lyophilizate Of 4-(2-Sulfo-ethylthio)cyclophosphamide-Lysine Salt (L-Lysine) With Citric Acid Lysine Buffer 1. An ion exchange column having a cooling jacket was loaded with 1300 ml of an acid ion exchanger, regenerated with 2 liters of 10% hydrochloric acid and washed with water suitable for injection purposes until neutral and free of chloride.
2. Subsequently the column was loaded with the help of 3 liters of a 10% lysine solution, free of excess lysine by washing with water suitable for injection purposes and washed until neutral.
3. There were passed over the column 1.4 liters of the following composition:

| | |
|---|---|
| 4-(sulfo-ethylthio)-cyclo-phosphamide cyclohexylamine salt | 137.12 g |
| Citric Acid, water free | 28.83 g |
| 1 N NaOH | 193.20 ml |
| Water for injection purposes | to 1.4 liter |

Active agents and adjuvant were dissolved in water of about 4° C. The pH of the solution was 4.1. The cation exchange column was then also cooled to about 4° C. The above solution was passed over the column. The flow through speed was 10 ml/minutes.

The eluate was caught in a cooled receiver, whereby the first 300 ml was discarded as forerunner. Subsequently the column was washed with water suitable for injection purposes and cooled to 4° C. and the entire volume of the eluate filled up to 3 liters.

The eluate which should be further processed to lyophilizate has the following composition:

| | |
|---|---|
| 4-(2-Sulfo-ethylthio)-cyclophosphamide Lysine salt (L-lysine) | 150.00 g |
| Citric Acid water free | 28.83 g |
| L-Lysine water free | 28.24 g |
| Water for injection purposes | 2870.93 g |
| | 3078.00 g |
| = | 3000 ml |

4. For the production of the lyophilizate the above solution was subjected to a sterile filtration in known manner. The receiving vessel was cooled. All the procedures following the sterile filtration were carried out under aseptic conditions.

The sterile solution was filled into injection flasks as follows:
2 ml of solution in a 10 ml injection flask.
The active material content is 100 mg.
10 ml of solution in a 30 ml injection flask.
The active material content is 500 mg.

The flasks were provided with sterile freeze drying stoppers and lyophilized in a freeze drying unit. Subsequently the unit was deaerated with sterile, dried nitrogen and the ampoule flasks closed in the unit.

For the production on appliable injection solution the contents of the flasks containing 100 mg of active material were dissolved in 5 ml of water suitable for injection purposes and the contents of the flasks containing 500 mg of active material were dissolved in 25 ml of such water.

(c) Example For The Production Of A Lyophilizate Of 4-Sulfo-ethylthiocyclophosphamide-Arginine Salt 90 grams of 4-sulfo-ethylthiocyclophosphamide-arginine salt and 135 grams of sodium-2-mercapto-ethane-sulfonate were dissolved with stirring in 1500 ml of water, cooled to 4° C. and suitable for injection purposes. After complete solution it was filled up to 1800 ml with water at 4° C. The pH was adjusted to about 4.2 with several particles of regenerated cation exchanger (H+ form). For the production of the lyophilizate the above solution was subjected to a sterile filtration in known manner. The receiving vessel was cooled. All of the procedures subsequent to the sterile filtration were carried out under aseptic conditions. The sterile solution was filled to 2 ml in a 10 ml injection flask. The content of active material is 100 mg. The flasks were provided with sterile freeze drying stoppers and lyophilized in a freeze drying unit. Subsequently the unit was deaerated with sterile, dried nitrogen and the ampoule flasks closed in the unit. For the production of an appliable injection solution the contents of the flasks were dissolved in 5 ml of water suitable for injection purposes.

The lyophilizate is stored at 0°–6° C. (refrigerator).

The entire disclosure of German application No. P 3407585.2 is hereby incorporated by reference.

What is claimed is:

1. A salt of oxazaphosphorine derivatives of the formula

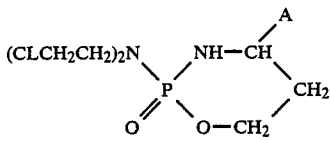

where A is the group —S—alk—SO$_3$H and alk represents a C$_2$–C$_4$-alkylene residue with a basic compound of the formula:

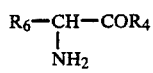

wherein R$_4$ is a hydroxy group or an amino group R$_6$ is hydrogen or a C$_1$–C$_6$-alkyl group or a C$_1$–C$_6$-alkyl group which is substituted by an amino group or a guanido group.

2. A salt according to claim 1 where A is ethylene.
3. A salt according to claim 2 of a compound of formula I with lysine, glycinamide or arginine.
4. A salt according to claim 1 of a compound of formula I with lysine, glycinamide, or arginine.
5. A drug containing a salt according to claim 1 and additionally a pharmaceutically acceptable carrier, diluent, or adjuvant.
6. A drug according to claim 5 additionally containing (1) a buffer or (2) the alkali salt of a mercapto-C$_2$–C$_6$-alkanesulfonic acid, or (3) both (1) and (2).
7. A drug containing a salt according to claim 1 and additionally a pharmaceutically acceptable carrier, diluent, adjuvant, buffer or the alkali salt of a mercapto-C$_2$–C$_6$-alkanesulfonic acid.

* * * * *